United States Patent [19]

Bach et al.

[11] Patent Number: 4,879,418

[45] Date of Patent: Nov. 7, 1989

[54] PROCESS FOR THE PREPARATION OF ALDEHYDES

[75] Inventors: Hanswilhelm Bach, Duisburg; Helmut Bahrmann, Hamminkeln-Brunen; Boy Cornils, Hofheim; Wilhelm Gick, Duisburg; Volker Heim, Oberhausen; Werner Konkol, Oberhausen; Ernst Wiebus, Oberhausen, all of Fed. Rep. of Germany

[73] Assignee: Hoechst Aktiengesellschaft, Fed. Rep. of Germany

[21] Appl. No.: 226,768

[22] Filed: Aug. 1, 1988

[30] Foreign Application Priority Data

Aug. 6, 1987 [DE] Fed. Rep. of Germany ...... 3726128

[51] Int. Cl.$^4$ .............................................. C07C 45/50
[52] U.S. Cl. ..................................... 568/454; 568/455
[58] Field of Search ............... 568/450, 455, 454, 451, 568/452

[56] References Cited

U.S. PATENT DOCUMENTS

| | | | |
|---|---|---|---|
| 3,928,232 | 12/1975 | Wilkes | 252/428 |
| 4,399,312 | 8/1983 | Russell et al. | 568/454 |
| 4,578,523 | 3/1986 | Bahrmann et al. | 568/454 |
| 4,795,727 | 1/1989 | Bach et al. | 568/454 |
| 4,801,754 | 1/1989 | Bach et al. | 568/454 |

OTHER PUBLICATIONS

European Search Report EP 88 11 2112 2 pages.

*Primary Examiner*—Werren B. Lone
*Attorney, Agent, or Firm*—Jordan B. Bierman

[57] ABSTRACT

A process for the preparation of aldehydes including reacting olefins with carbon monoxide and hydrogen in an aqueous liquid phase in the presence of a rhodium catalyst and a specific class of water soluble aryl phosphines. These phosphines are preferably mixtures of alkali metal salts and quaternary ammonium salts of sulfonated aryl phosphines.

36 Claims, No Drawings

PROCESS FOR THE PREPARATION OF ALDEHYDES

The present invention relates to a process for the preparation of aldehydes through hydroformylation of olefins in the presence of water-soluble rhodium complex catalysts.

BACKGROUND OF THE INVENTION

It is known to prepare aldehydes and alcohols by reacting olefins with carbon monoxide and hydrogen. The reaction is catalyzed by hydridometal carbonyls, preferably those of metals of group VIII of the Periodic Table. In addition to cobalt, which is used extensively in industry as a catalyst metal, rhodium has recently become increasingly important. In contrast to cobalt, rhodium permits the reaction to be carried out at low pressure; also, straight-chain n-aldehydes are formed preferentially, and iso-aldehydes only to a minor extent. Finally, the hydrogenation of olefins to form saturated hydrocarbons occurs to a considerably lesser extent when rhodium catalysts are used than when cobalt catalysts are used.

In the processes which have been introduced into industry, the rhodium catalyst is employed in the form of modified hydridorhodium carbonyls which additionally and optionally contain excess ligands. Ligands which have proven particularly successful are tertiary phosphines or phosphites. Use of these compounds enables the reaction pressure to be reduced to values below 30 MPa.

However, the separation of the reaction products and recovery of the catalyst dissolved homogeneously in the reaction product cause problems. In general, separation is effected by removing the reaction product from the reaction mixture by distillation. In practice, however, this method can only be used in the hydroformylation of lower olefins having up to about 8 carbon atoms in the molecule, due to the thermal sensitivity of the aldehydes and alcohols formed. In addition, it has become apparent that heating of the distillation material also leads to considerable losses in catalyst through decomposition of the rhodium complex compounds.

The problems described are avoided by using catalyst systems which are soluble in water. Such catalysts are described, for example, in German Patent 2,627,354. The solubility of the rhodium complex compounds is achieved there by using sulfonated triarylphosphines as the complex component. The removal of the catalyst from the reaction product, when the hydroformylation reaction is complete, is effected simply by separating the aqueous and organic phases, i.e. without distillation and thus without additional thermal steps. A further feature of this procedure is that n-aldehydes are formed with high selectivity from terminal olefins, and iso-aldehydes are formed only to a very minor extent. Besides sulfonated triarylphosphines, carboxylated triarylphosphines are also employed as the complex components of water-soluble rhodium complex compounds.

The known two-phase processes have proven highly successful in the hydroformylation of lower olefins, in particular ethylene and propylene. If higher olefins, such as octene or decene, are employed, the conversion and/or selectivity for n-compounds drops markedly. Hence, on an industrial scale, the reaction is frequently no longer economical.

Various methods have been used to overcome these difficulties. According to DE 3,412,335 A1, a solubilizer is added to the reaction medium. A disadvantage of this procedure is the use of reagents which are alien to the reaction, i.e. are not among the starting materials, the reaction products, or the catalytic substances. This means that a negative effect on the reaction proceedings and, in particular, on the life of the catalysts cannot be excluded.

The process described in DE 3,420,491 A1 for hyroformylation of olefins uses catalytically active rhodium complex compounds in which the complex ligands are quaternary ammonium salts of sulfonated triarylphosphines. The quaternary ammonium ions contain an alkyl or aralkyl radical having 7 to 18 carbon atoms and 3 straight or branched alkyls having 1 to 4 carbon atoms. This process has also proven very successful in the reaction of higher olefins. However, the high price of quaternary ammonium hydroxides, which are necessary for recovery of the quaternary ammonium salts of sulfonated triarylphosphines, stands in the way of its general use.

DETAILED DESCRIPTION OF THE INVENTION

The present invention is a process for the preparation of aldehydes based upon the reaction of olefins with carbon monoxide and hydrogen in an aqueous liquid phase in the presence of a rhodium catalyst and a water soluble phosphene. The catalyst can be in the form of a metal or a compound. The phosphine is of the formula

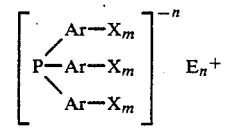

wherein each Ar is aryl. These may be the same or different. X is a sulfonic acid group and E is an alkali metal ion or a quaternary ammonium ion of the formula

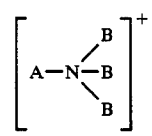

wherein A is a branched or straight chain higher alkyl and each B is a branched or straight chain lower alkyl. The letter m represents 0 or 1 and n is an integer from 1 to 3.

It is preferred that the process be carried out at temperatures from 20° to 150° C. and pressures of 0.1 to 20 MPa. The more preferred reaction temperatures are 50° to 120° C. and the preferred pressures are 0.1 to 10 MPa and the most preferred pressures are 0.1 to 5 MPa.

It has been found that sodium and/or potassium are particularly suitable as E in the general formula. Ar may advantageously be phenyl or naphthyl, preferably phenyl. It is also desirable that the sum of the m's be 2 or 3.

The presence of the rhodium catalyst in an amount of 10 to 2,000 ppm by weight based on the aqueous catalyst solution has been found to be particularly useful. It is preferable that the catalyst concentration be in the range of 50 to 800 ppm.

The catalyst may be a finely divided metal or water soluble rhodium salts or compounds. More specifically, such water soluble salts as rhodium chloride, rhodium sulfate, and rhodium acetate have been found useful. On the insoluble side, rhodium hexanoate and rhodium oxides are worthy of particular mention.

The phosphine may desirably be present in an amount of 2 to 300 moles, preferably 1 to 100 moles, per gram atom of rhodium. The pH should be at least 2, preferably 2.0 to 13.0, and most preferably from 5.0 to 7.0. Control of the pH may be by use of a known buffer. This can be present in an amount of 1 to 20%, preferably 3 to 10%, of the catalyst solution.

The carbon monoxide and hydrogen are usually introduced as synthesis gas. The ratios of monoxide to hydrogen may vary widely, but an approximately equal ratio is desirable. The olefins treated are those which preferably have at least 8 carbon atoms, more preferably those having 10 to 20 carbon atoms.

Particularly useful phosphines are the sodium or potassium salts of trisulfonated triphenyl phosphine, disulfonated triphenyl phosphine, and tetraalkyl salts of sulfonated triphenyl phosphine. These phosphines are reacted with cations taken from the class consisting of trimethylcetyl ammonium, trimethyldecyl ammonium, trimethyltetradecyl ammonium, trimethylhexadecyl ammonium, and dodecylethyldimethyl ammonium.

Insofar as the quaternary ion is concerned, A advantageously has 6 to 20 carbon atoms, preferably 10 to 18 carbon atoms, and most preferably 12 to 16 carbon atoms. B preferably has 1 to 4 carbon atoms, and methyl and/or ethyl are particularly desirable.

It has been found that it is not necessary to use quaternary ammonium salts of sulfonated triarylphosphines as the complex ligands for rhodium to successfully convert higher olefins into aldehydes by hydroformylation. It is both surprising and unsuggested by the prior art that mixtures of alkali metal salts and small amounts of quaternary ammonium salts are satisfactory for this purpose. The quaternary ammonium ions of the present invention contain a high carbon atom alkyl and three lower alkyl radicals. These radicals may be branched or unbranched as desired. The phosphines of the present invention are prepared by sulfonation of triarylphosphines with oleum. Variations in reaction conditions permit preferential preparation of the mono-, di-, or trisulfonated aryl phosphines. More specifically, control of reaction time, reaction temperature, and triaryl phosphine:sulfur trioxide ratio are of particular importance in this regard. However, the parameters necessary for the production of any particular phosphine are known to those of ordinary skill. Initially, the reaction produces amine salts which are insoluble in water but soluble in organic solvents. These products are thereafter converted into the desired onium salt of the sulfonated triarylphosphine by treatment with a quaternary ammonium hydroxide.

The catalyst can be prepared outside the reaction system and added thereto in completed form. However, it can also be prepared in situ in the presence of the olefin. In this case, the rhodium (as metal or in the form of a compound) and the aqueous solution of the quaternary ammonium salt of the sulfonated triarylphosphine are added to the reaction system, thereby forming the desired catalyst.

Since it is useful to maintain the pH in the desired range, buffer solutions may also be included in the formulation. A mixture of sodium acetate and acetic acid is suitable for this purpose. It is usually added to the aqueous phase in an amount of 1 to 20% by weight, based on the entire aqueous solution. Preferably, 3 to 10% by weight is used. The process can be carried out either batchwise or continuously.

The olefins used may be straight or branched chain, and those having at least 8 carbon atoms are particularly useful. Olefins having 10 to 20 carbon atoms are particularly preferred. The unsaturation may be terminal or internal.

The following examples are illustrative in nature and are not intended to limit the Invention.

EXAMPLES 1 TO 5

Sodium salts of triphenyl phosphine m-disulfonic acid and triphenylphosphine m-trisulfonic acid (TPPTA-Na) in a ratio of 1:10, an onium salt, a buffer, and rhodium acetate were introduced into a one liter autoclave provided with a dip tube. The onium salt was the amine derivative of the aforementioned TTPTA-Na. The buffer solution contained 3 moles of sodium acetate and 0.3 moles of acidic acid. 400 ppm of rhodium was present in the form of the acetate.

Synthesis gas ($CO/H_2 = 1:1$) was then introduced to create a pressure of 2.5 MPa. The reaction solution was treated with the synthesis gas for three hours at 125° C. with stirring. Thereafter, the mixture was cooled to approximately 30° C., the stirring was stopped and, after allowing the mixture to settle for 15 minutes, the excess solution was forced out through the dip tube and analyzed. The residual solution remained in the autoclave.

With stirring, n-hexene-1 is pumped in by means of a pressure pump. The mixture is then heated to 125° C. for 3 hours, maintaining a pressure of 2.5 MPa. The mixture is then cooled to 30° C. and allowed to settle. After 15 minutes, the supernatant organic phase is forced out through the dip tube. This phase is then weighed and analyzed by gas chromatography.

The various materials introduced and results thereof are shown in Tables 1 and 2 herein.

The term "activity" is defined as $$A = \frac{\text{moles of aldehyde}}{\text{g/atom of Rh} \times \text{min}}$$

"productivity" is defined as $$P = \frac{\text{grams of aldehyde}}{\text{ml of catalyst solution} \times \text{h}}$$

In addition to the foregoing, the n-aldehyde: i-aldehyde ratio is set forth. It has been found that the hydrocarbons and alcohols formed are negligible in all cases.

Although only a limited number of specific embodiments of the present invention have been expressly disclosed, it is, nonetheless, to be broadly construed, and not to be limited except by the character of the claims appended hereto.

TABLE 1

|  | Example 1 | Example 2 | Example 3 | Example 4 | Example 5 |
| --- | --- | --- | --- | --- | --- |
| TPPTA-Na sol. (g) | 413 | 431 | 438 | 440 | 560 |
| Buffer sol. (g) | 23 | 25 | 31 | 25 | 30 |
| P(III) content of the catalyst sol (mol/kg) | 0.324 | 0.374 | 0.330 | 0.364 | 0.393 |
| Amount of hexene (g) | 175 | 175 | 175 | 175 | 200 |

TABLE 2

| | Reaction parameters | | | | |
| --- | --- | --- | --- | --- | --- |
| | 100 mol % of TPPTA-Na | 92.5 mol % of TPPTA-Na + 7.5 mol % of TPPTA-NR$_4$ | | | |
| | Example 1 Na* | Example 2 Bu$_4$N* | Example 3 C$_{12}$H$_{25}$Me$_3$N* | Example 4 C$_{14}$H$_{29}$Me$_3$N* | Example 5 C$_{16}$H$_{31}$Me$_3$N* |
| Conversion (%) | 22 | 37 | 56 | 73 | 56 |
| Productivity | 0.035 | 0.059 | 0.096 | 0.127 | 0.110 |
| Activity | 1.18 | 2.0 | 3.4 | 4.41 | 2.8 |
| n/i ratio | 98/2 | 98/2 | 92/8 | 93/7 | 91/9 |

Me = —CH$_3$
Bu = —C$_4$H$_9$

What we claim is:

1. The process for the preparation of aldehydes comprising reacting at least one olefin of 2 to 20 carbon atoms with carbon monoxide and hydrogen in the liquid phase in the presence of water, a catalyst comprising rhodium in metallic form or as a compound and at least one water soluble phosphine of the formula

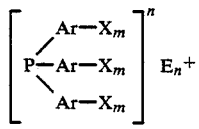

wherein each Ar is an aryl radical, X is a sulfonic acid group, and E is a mixture of an alkali metal ion or ammonium ion and a quaternary ammonium ion of the formula

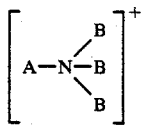

wherein A is an alkyl of 6 to 20 carbon atoms and each B is individually an alkyl of 1 to 4 carbon atoms, each m is 0 or 1 and n is an integer from 2 to 3.

2. The process of claim 1 wherein all Ar's are the same.
3. The process of claim 1 carried out at a reaction temperature of 20° to 150° C.
4. The process of claim 3 wherein said temperature is 50° to 120° C.
5. The process of claim 1 carried out under a pressure of 0.1 to 20 MPa.
6. The process of claim 5 wherein said pressure is 0.1 to 10 MPa.
7. The process of claim 6 wherein said pressure is 0.1 to 5 MPa.
8. The process of claim 1 wherein said ammonium ion comprises 1 to 30 mol % of said phosphine.
9. The process of claim 8 wherein said ammonium ion comprises 3 to 15 mol % based on said phosphine.
10. The process of claim 9 wherein said ammonium ion comprises 5 to 10 mol % of said phosphine.
11. The process of claim 1 wherein E is sodium and/or potassium.
12. The process of claim 1 wherein A and B are unbranched.
13. The process of claim 1 wherein A has from 10 to 18 carbon atoms.
14. The process of claim 13 wherein A has from 12 to 16 carbon atoms.
15. The process of claim 1 wherein B is methyl and/or ethyl.
16. The process of claim 1 wherein Ar is phenyl or naphthyl.
17. The process of claim 16 wherein Ar is phenyl.
18. The process of claim 1 wherein the sum of all the m's is 2 or 3.
19. The process of claim 1 wherein said phosphine is taken from the class consisting of sodium or potassium salts of trisulfonated triphenyl phosphine, disulfonated triphenyl phospine, and tetraalkyl salts of sulfonated triphenyl phosphines combined with cations from the class consisting of trimethylethyl ammonium, trimethyldodecyl ammonium, trimethyltetradicyclo ammonium, trimethylhexadecyl ammonium, and dodecylethyldimethyl ammonium.
20. The process of claim 1 wherein said rhodium is 10 to 2000 ppm by weight based on the aqueous catalyst solution.
21. The process of claim 20 wherein said rhodium is 50 to 800 ppm by weight based on the aqueous catalyst solution.
22. The process of claim 1 wherein said rhodium is in finely divided metallic form.
23. The process of claim 1 wherein said rhodium is in the form of water soluble rhodium salts or compounds.
24. The process of claim 23 wherein said water soluble rhodium salts are taken from the class consisting of rhodium chloride, rhodium sulfate, and rhodium acetate.
25. The process of claim 1 wherein said rhodium is in the form of rhodium hexanoate or rhodium oxides.
26. The process of claim 1 wherein there are 2 to 300 mols of said phosphine per gram atom of rhodium.
27. The process of claim 26 wherein there are 1 to 100 mols of said phosphine per gram atom of rhodium.
28. The process of claim 1 carried at a pH of at least 2.